US00PP24780P3

(12) United States Plant Patent
Korlipara

(10) Patent No.: US PP24,780 P3
(45) Date of Patent: Aug. 19, 2014

(54) *RODGERSIA* PLANT NAMED 'BRONZE PEACOCK'

(50) Latin Name: *Rodgersia pinnata*
Varietal Denomination: Bronze Peacock

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 299 days.

(21) Appl. No.: 13/506,756

(22) Filed: May 14, 2012

(65) Prior Publication Data

US 2013/0305421 P1 Nov. 14, 2013

(51) Int. Cl.
*A01H 5/00* (2006.01)

(52) U.S. Cl.
USPC ..... Plt./226

(58) Field of Classification Search
USPC ..... Plt./226, 263.1
See application file for complete search history.

*Primary Examiner* — Kent L Bell
(74) *Attorney, Agent, or Firm* — Klarquist Sparkman, LLP

(57) ABSTRACT

A new and distinct *Rodgersia* plant characterized by exceptionally dark and shiny spring leaves, dark tinted new leaves and leaf edges in summer, and excellent vigor.

1 Drawing Sheet

Botanical denomination: *Rodgersia pinnata.*
Variety designation: 'Bronze Peacock'.

BACKGROUND OF THE INVENTION

The present invention relates to a new and distinct cultivar of *Rodgersia pinnata* and given the cultivar name of 'Bronze Peacock'. *Rodgersia* is in the family Saxifragaceae. *Rodgersia* 'Bronze Peacock' originated as a naturally occurring tissue culture mutation of *Rodgersia pinnata* 'Ideal', an unpatented plant.

Compared to the parent, *Rodgersia pinnata* 'Ideal', the new cultivar has much darker spring and summer leaves and a shorter habit.

Compared to *Rodgersia pinnata* 'Chocolate Wing', an unpatented plant, the new cultivar has smaller, thicker leaves and leaflets and much darker spring and summer leaves and shorter habit.

This new *Rodgersia* is uniquely distinguished by:

1. exceptionally dark and shiny spring leaves,
2. dark tinted new leaves and leaf edges in summer,
3. and excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a 2 year-old plant of *Rodgersia* 'Bronze Peacock' growing outside in the ground in May in a shade house in Canby, Oreg.

FIG. 2 shows *Rodgersia* 'Bronze Peacock' growing in the ground in flower in early June in Canby, Oreg.

DETAILED PLANT DESCRIPTION

The following is a detailed description of the new *Rodgersia* cultivar based on observations of 2-year-old specimens growing in one gallon containers in a cold greenhouse in March in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The *Royal Horticultural Society Colour Chart,* 1999 edition, 5$^{th}$ edition.

Plant:

*Form.*—Stout, rhizomatous, herbaceous perennial.
*Hardiness.*—USDA Zone 5 to 8.
*Size.*—30 cm tall from top of the foliage to the soil and 56 cm wide.
*Habit.*—Mounding.
*Vigor.*—Excellent.

Leaf:

*Type.*—Palmately compound to pseudo-pinnate.
*Arrangement.*—Basal.
*Shape.*—Orbicular.
*Leaflets.*—5 to 7 in number, grow to 20 mm long and 13 mm wide, obovate in shape, with veins pinnate, margins serrate, apex acute, base attenuate.
*Base.*—Cordate.
*Blade size.*—Grows to 34 cm long and 34 cm wide.
*Texture.*—Leathery.
*Surface texture.*—Pubescent on top and bottom side.
*Petiole description.*—Grows to 30 cm long and 6 mm wide, pubescent, Yellow Green 145C tinted Greyed Purple 187C.
*Leaf color.*—Topside spring Greyed Purple 187A, with main vein Greyed Purple 187C; bottom side Greyed Green 191C with veins Greyed Purple 187B; summer leaves Green 137A with main vein Yellow Green 145C and with margins tinted Greyed Purple 187A, bottom side Yellow Green 147B with margins Greyed Purple 187A and main vein Yellow Green 145C tinted Greyed Purple 187A near base.

Inflorescence:

*Size.*—Grows to 10 cm wide and 31 cm long.

*Type.*—Dense panicle.

*Number of flowers per panicle.*—About 180.

*Number of panicles.*—About 3.

*Peduncle.*—Grows to 43 cm long, 7 mm wide at base, leafy with swollen leaf nodes (floral leaves grow to 20 cm long and 20 cm wide, with one to 5 leaflets), Greyed Purple 187B, glandular hairs.

*Pedicel.*—0 to 4 mm long, pubescent, Red 36A.

*Bloom period.*—Mid June to early July in Canby, Oreg.

Flower bud:

*Size.*—4 mm wide and 4 mm long.

*Description.*—Glandular puberulent, ovoid.

*Color.*—Red 51A.

Flower:

*Type.*—Perfect.

*Shape.*—Stellate.

*Size.*—7 mm deep and 12 mm wide.

*Corolla description.*—None.

*Calyx description.*—Stellate, 2 mm deep and 12 mm wide, with 5 to 6 lobes divided ½ way to the base, each 4 mm wide and 4 mm long, pubescent outside and glabrous inside, tips mucronulate, margin entire; color overall Red Purple 62B, but in detail outside and inside color Red Purple 67A on top half of lobe (Greyed Purple 187A on very tip) and White NN155D on tube and bottom half of lobes.

*Stamen description.*—10 to 12 in number, 4 mm long, filaments 3.7 mm long and Red Purple 62D, anthers Greyed Purple N187A, pollen Yellow 11D.

*Pistil description.*—1, 3-beaked, 5 mm deep and 4 mm wide, ovary 4 mm long and 4 mm wide, Red Purple 62C, style 2.2 mm long, Red Purple 62D, stigma Red Purple N66D.

*Fragrance.*—Sweet.

*Lastingness.*—Each panicle blooms for about 5 weeks on the plant.

Pest and disease tolerance: The new cultivar is typical to the genus. No known resistances to pests or diseases. No problems have been found in Canby, Oreg.

I claim:

1. A new and distinct *Rodgersia* plant as herein illustrated and described.

* * * * *

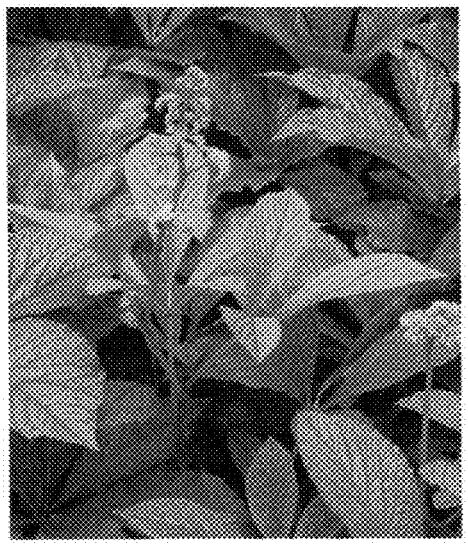

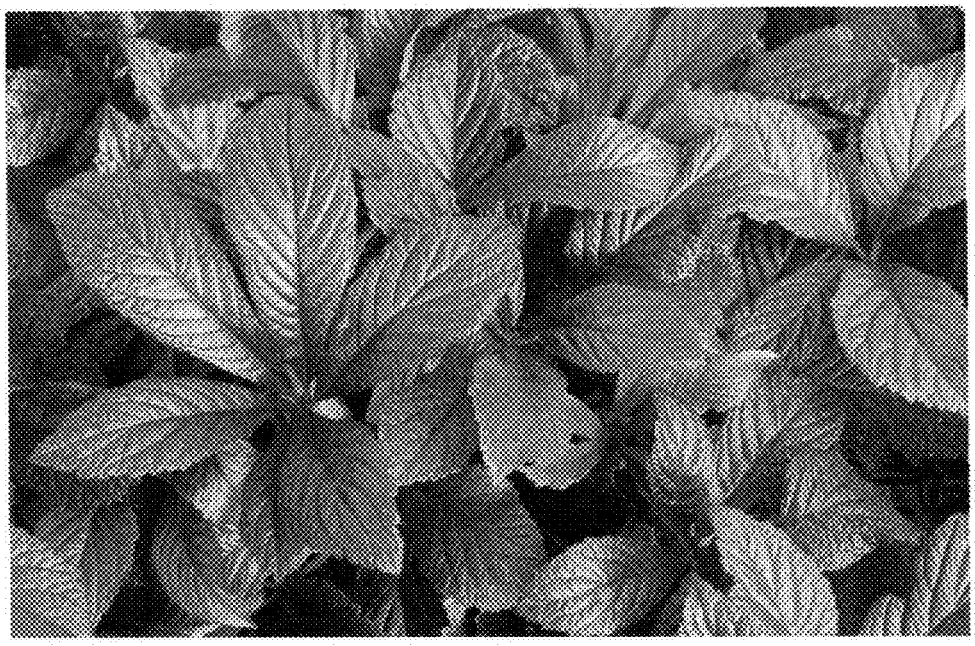
FIG, 1 above
FIG. 2 to right